US012702351B2

(12) United States Patent
Chung et al.

(10) Patent No.: US 12,702,351 B2
(45) Date of Patent: Aug. 11, 2026

(54) DIABETIC FOOT ANALYSIS APPARATUS, AND DIABETIC FOOT MANAGEMENT SYSTEM

(71) Applicants: SEOUL NATIONAL UNIVERSITY HOSPITAL, Seoul (KR); HIPPO T&C, INC., Gyeonggi-do (KR); RESEARCH & BUSINESS FOUNDATION SUNGKYUNKWAN UNIVERSITY, Gyeonggi-do (KR)

(72) Inventors: Tai Myoung Chung, Seoul (KR); Chan Yeong Heo, Gyeonggi-do (KR); Ji Ung Park, Seoul (KR); Min Ha Choi, Gyeonggi-do (KR)

(73) Assignees: SEOUL NATIONAL UNIVERSITY HOSPITAL, Seoul (KR); HIPPO T&C, INC., Gyeonggi-Do (KR); RESEARCH & BUSINESS FOUNDATION SUNGKYUNKWAN UNIVERSITY, Gyeonggi-Do (KR)

( * ) Notice: Subject to any disclaimer, the term of this patent is extended or adjusted under 35 U.S.C. 154(b) by 340 days.

(21) Appl. No.: 18/273,327

(22) PCT Filed: Jan. 19, 2022

(86) PCT No.: PCT/KR2022/000978
§ 371 (c)(1),
(2) Date: Jul. 20, 2023

(87) PCT Pub. No.: WO2022/158848
PCT Pub. Date: Jul. 28, 2022

(65) Prior Publication Data

US 2024/0115191 A1 Apr. 11, 2024

(30) Foreign Application Priority Data

Jan. 20, 2021 (KR) ........................ 10-2021-0008365

(51) Int. Cl.
*A61B 5/00* (2006.01)
*A61B 5/0205* (2006.01)
(Continued)

(52) U.S. Cl.
CPC ............ *A61B 5/445* (2013.01); *A61B 5/0002* (2013.01); *A61B 5/02055* (2013.01);
(Continued)

(58) Field of Classification Search
CPC ... A61B 5/445; A61B 5/0002; A61B 5/02055; A61B 5/1036; A61B 5/1116;
(Continued)

(56) References Cited

U.S. PATENT DOCUMENTS

2009/0234262 A1 9/2009 Reid, Jr. et al.
2012/0109013 A1* 5/2012 Everett ................ A61B 5/1036 600/587

(Continued)

FOREIGN PATENT DOCUMENTS

KR 10-1004001 B1 12/2010
KR 10-2015-0078879 A 7/2015

(Continued)

OTHER PUBLICATIONS

International Search Report for PCT/KR2022/000978 mailed on Apr. 22, 2022.

*Primary Examiner* — Rex R Holmes
(74) *Attorney, Agent, or Firm* — PLEECHAE IP, LLC

(57) ABSTRACT

A diabetic foot management system according to one aspect includes a diabetic foot monitoring apparatus configured to measure user's foot condition information; and a diabetic foot analysis apparatus configured to determine a degree of progression of user's diabetic foot ulcer from the measured
(Continued)

foot condition information using a machine learning-based diabetic foot determination model.

11 Claims, 4 Drawing Sheets

(51) Int. Cl.

| | |
|---|---|
| ***A61B 5/103*** | (2006.01) |
| ***A61B 5/11*** | (2006.01) |
| *A61B 5/026* | (2006.01) |
| *A61B 5/145* | (2006.01) |

(52) U.S. Cl.
CPC .......... *A61B 5/1036* (2013.01); *A61B 5/1116* (2013.01); *A61B 5/4836* (2013.01); *A61B 5/4842* (2013.01); *A61B 5/6807* (2013.01); *A61B 5/7267* (2013.01); *A61B 5/026* (2013.01); *A61B 5/14532* (2013.01); *A61B 5/14542* (2013.01)

(58) Field of Classification Search
CPC ... A61B 5/4836; A61B 5/4842; A61B 5/6807; A61B 5/7267; A61B 5/026; A61B 5/14532; A61B 5/14542; A61B 5/1038; A61B 5/14551; A61B 5/447; A61B 5/6829; A61B 5/14517; A61B 5/14539; A61F 2007/0045; A61F 2007/0088; A61F 7/02; A61H 2205/12; A61H 2230/202; A61H 2230/203; A61H 2230/208; A61H 23/02; A61N 2005/0659
See application file for complete search history.

(56) References Cited

U.S. PATENT DOCUMENTS

| | | | | |
|---|---|---|---|---|
| 2015/0133754 | A1* | 5/2015 | Freeman ................. | A61F 2/586 600/407 |
| 2016/0206242 | A1* | 7/2016 | Esposito .............. | A61B 5/1038 |
| 2018/0249945 | A1* | 9/2018 | Najafi .................... | A61B 5/112 |
| 2020/0193597 | A1* | 6/2020 | Fan ...................... | H04N 25/135 |
| 2020/0275864 | A1* | 9/2020 | Heikenfeld ........ | A61B 5/14517 |

FOREIGN PATENT DOCUMENTS

| | | | |
|---|---|---|---|
| KR | 10-2016-0131823 | A | 11/2016 |
| KR | 10-2020-0097447 | A | 8/2020 |
| WO | WO 2012/055029 | A1 | 5/2012 |

* cited by examiner

DIABETIC FOOT ANALYSIS APPARATUS, AND DIABETIC FOOT MANAGEMENT SYSTEM

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2022/000978, filed Jan. 19, 2022, which claims priority to the benefit of Korean Patent Application No. 10-2021-0008365 filed in the Korean Intellectual Property Office on Jan. 20, 2021, the entire contents of which are incorporated herein by reference.

BACKGROUND

1. Technical Field

The present invention relates to a diabetic foot analysis apparatus and a diabetic foot management system.

2. Background Art

Diabetic foot ulcer, a serious complication occurring in diabetic patients, is a representative chronic wound accompanied by non-healing infection. 15% or more of patients suffering from diabetes develop diabetic foot ulcers, and one million or more patients a year are subjected to lower extremity amputation due to the non-healing wound.

According to the report of the Korean Diabetes Association, 44.8% of patients with foot amputation in 2003 also had diabetes, and it has been reported that an incidence rate of foot amputations in diabetic patients is times higher than non-diabetic individuals. Diabetic peripheral neuropathy and occlusion of peripheral blood vessels are the major causes of an incidence of diabetic foot ulcers in patients with poorly controlled diabetes. Most chronic diabetic patients have poor treatment compliance, such that it is difficult to prevent diabetic neuropathy and diabetic foot ulcers only with a medical examination at a hospital.

SUMMARY

An object of the present invention is to provide a diabetic foot analysis apparatus and a diabetic foot management system.

To achieve the above object, according to an aspect of the present invention, there is provided a diabetic foot management system including: a diabetic foot monitoring apparatus configured to measure user's foot condition information; and a diabetic foot analysis apparatus configured to determine a degree of progression of user's diabetic foot ulcer from the measured foot condition information using a machine learning-based diabetic foot determination model.

The diabetic foot monitoring apparatus may include a blood glucose measurement sensor, a pressure measurement sensor, a blood flow measurement sensor, and a transcutaneous oxygen saturation measurement sensor, and the foot condition information may include blood glucose information, pressure information, blood flow information, and transcutaneous oxygen saturation information, which are measured from a user's foot.

The blood glucose measurement sensor, the blood flow measurement sensor, and the transcutaneous oxygen saturation measurement sensor may be placed on a longitudinal arch portion.

The pressure measurement sensor may be placed on both sides of the front of a sole (greater ball, lesser ball) or a heel portion.

The blood glucose measurement sensor may measure blood glucose using user's sweat.

The diabetic foot monitoring apparatus may further include at least one of a temperature measurement sensor, a humidity measurement sensor, a pH measurement sensor, and a matrix metalloproteinase measurement sensor, and the foot condition information may further include at least one of skin temperature information, skin humidity information, pH information, and matrix metalloproteinase information, which are measured from the user's foot.

The temperature measurement sensor and the humidity measurement sensor may be placed on a toe pulp tip portion or a web space portion.

The pH measurement sensor and the matrix metalloproteinase measurement sensor may be placed on a skin defect portion due to diabetic foot wounds.

The diabetic foot monitoring apparatus may include at least one of a warmer configured to apply heat to the user's foot, a blood flow promoter configured to promote blood flow in the user's foot, and a pressure dispensing device configured to generate vibration to disperse a pressure applied to the user's foot.

The diabetic foot analysis apparatus may generate a foot improvement control signal for controlling the warmer, the blood flow promoter, and the pressure dispensing device based on the user's foot condition information and the degree of progression of the diabetic foot ulcer.

The diabetic foot monitoring apparatus may be implemented as an insole type or a shoe type apparatus.

The diabetic foot analysis apparatus may determine a user's posture and determine the degree of progression of the user's diabetic foot ulcer further using the determined user's posture.

The posture may include standing, sitting, walking, and running.

The diabetic foot analysis apparatus may determine the user's posture using the user's foot condition information.

According to another aspect of the present invention, there is provided a diabetic foot analysis apparatus including: a communication unit configured to receive user's foot condition information; a storage unit configured to store a machine learning-based diabetic foot determination model; and a processor configured to determine a degree of progression of user's diabetic foot ulcer based on the received foot condition information using the diabetic foot determination model.

The diabetic foot determination model may be established using foot condition information of a plurality of diabetic patients, and degrees of progression of the diabetic foot ulcers corresponding thereto as learning data.

The foot condition information may include blood glucose information, pressure information, blood flow information, transcutaneous oxygen saturation (TcPO2) information, temperature information, humidity information, pH information, and matrix metalloproteinase information, which are measured from a user's foot.

The processor may determine the user's posture and determine the degree of progression of the user's diabetic foot ulcer further using the determined user's posture.

The posture may include standing, sitting, walking, and running.

The processor may determine the user's posture using the user's foot condition information.

By performing functions to improve user's foot condition by measuring user's foot condition information through an insole type or shoe type diabetic foot monitoring apparatus and determining the degree of progression of the diabetic foot ulcer from the measured foot condition information by using machine learning, it is possible to prevent an incidence of the diabetic foot ulcers and manage the same.

DETAILED DESCRIPTION

Figure 1:
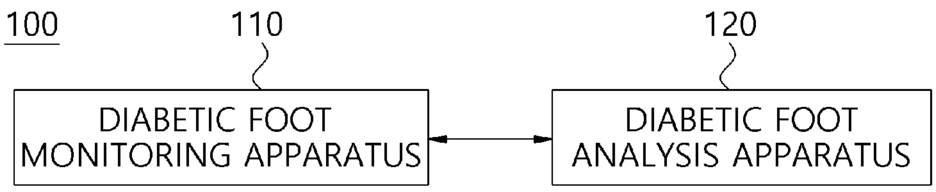
FIG. 1 is a block diagram illustrating an embodiment of a diabetic foot management system.

Hereinafter, embodiments will be described in detail with reference to the accompanying drawings. In denoting reference numerals to components of respective drawings, it should be noted that the same components will be denoted by the same reference numerals although they are illustrated in different drawings.

In descriptions of the embodiments, publicly known techniques related to the present invention, which are judged to be able to make the purport of the present invention unnecessarily obscure, will not be described in detail. In addition, the terms as used herein are defined by taking functions of the present invention into account and can be changed according to the custom or intention of users or operators. Therefore, definition of the terms should be made according to the overall disclosure set forth herein.

It will be understood that, although the terms first, second, etc. may be used herein to describe various components, but these components should not be limited by these terms. These terms are used only to distinguish one component from other components. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

In addition, a division of the configuration units in the present disclosure is intended for ease of description and divided only by the main function set for each configuration unit. That is, two or more of the configuration units to be described below may be combined into a single configuration unit or formed by two or more of divisions by function into more than a single configuration unit. Further, each of the configuration units to be described below may additionally perform a part or all of the functions among functions set for other configuration units other than being responsible for the main function, and a part of the functions among the main functions set for each of the configuration units may be exclusively taken and certainly performed by other configuration units.

Figure 2:
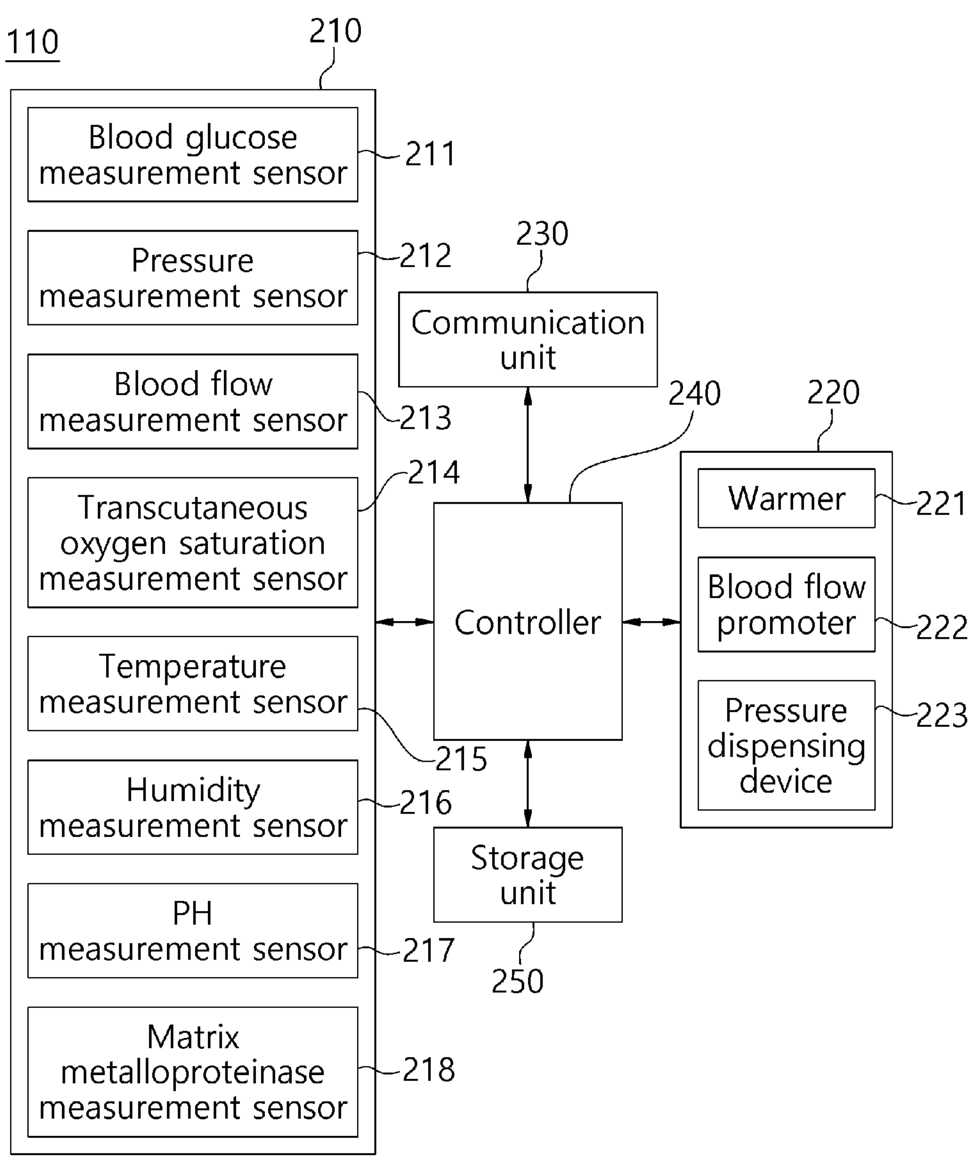
FIG. 2 is a block diagram illustrating an embodiment of an insole type diabetic foot monitoring apparatus.
Figure 3:
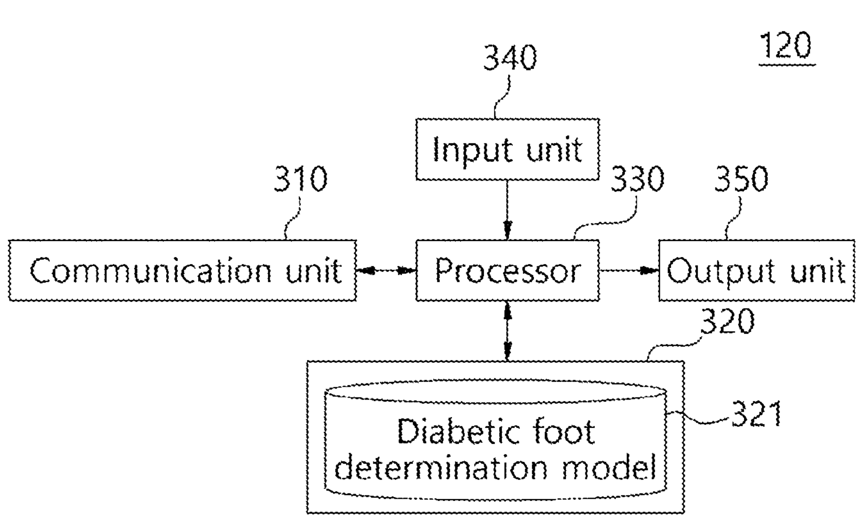
FIG. 3 is a block diagram illustrating an embodiment of a diabetic foot analysis apparatus.

FIG. 1 is a block diagram illustrating an embodiment of a diabetic foot management system, FIG. 2 is a block diagram illustrating an embodiment of an insole type diabetic foot monitoring apparatus, and FIG. 3 is a block diagram illustrating an embodiment of a diabetic foot analysis apparatus.

Referring to FIGS. 1 to 3, a diabetic foot management system 100 may include a diabetic foot monitoring apparatus 110 and a diabetic foot analysis apparatus 120.

The diabetic foot monitoring apparatus 110 is implemented as an insole type or a shoe type apparatus, and may perform functions of measuring user's foot condition information and improving user's foot conditions. To this end, the diabetic foot monitoring apparatus 110 may include a sensor unit 210, an improvement unit 220, a communication unit 230 and a controller 240.

The sensor unit 210 may measure user's foot condition information under the control of the controller 240. The user's foot condition information may include blood glucose information, pressure information, blood flow information, transcutaneous oxygen saturation (TcPO2) information, temperature information, humidity information, pH information, and matrix metalloproteinase information, which are measured at a user's foot. To this end, the sensor unit 210 may include a blood glucose measurement sensor 211, a pressure measurement sensor 212, a blood flow measurement sensor 213, a transcutaneous oxygen saturation measurement sensor 214, a temperature measurement sensor 215, a humidity measurement sensor 216, a pH measurement sensor 217 and a matrix metalloproteinase measurement sensor 218.

The blood glucose measurement sensor 211 may be placed on a longitudinal arch portion of user's inner sole to measure a user's blood glucose. For example, the blood glucose measurement sensor 211 may collect user's sweat from the user's foot and measure the user's blood glucose from the collected sweat. In this case, the blood glucose measurement sensor 211 may use an optical method of measuring blood glucose by irradiating sweat with a light, or an electrochemical method of measuring blood glucose based on a current generated in a process in which glucose reacts with an enzyme.

The pressure measurement sensor 212 may be placed on both sides of the front of a sole (greater ball, lesser ball) or a heel portion, which are portions where excessive keratin or osteophyte, a factor that causes joint deformity and diabetic foot ulcers, frequently occurs, to measure a pressure applied to the user's sole.

The blood flow measurement sensor 213 may be placed on a longitudinal arch portion or an instep portion of the user's inner sole to measure a user's blood flow. According to one embodiment, the blood flow measurement sensor 213 may use an optical method of measuring blood flow by irradiating the user's foot with a light (e.g., infrared rays) and receiving the light reflected from a subject.

The transcutaneous oxygen saturation measurement sensor 214 may be placed on a longitudinal arch portion or an instep portion of the user's inner sole to measure a user's transcutaneous oxygen saturation (TcPO2). According to one embodiment, the transcutaneous oxygen saturation measurement sensor 214 may use an optical method of measuring the transcutaneous oxygen saturation by irradiating the user's foot with a light (e.g., infrared rays) and receiving the light reflected from the subject.

The temperature measurement sensor 215 may be placed on a toe pulp tip and/or web space portion where skin temperature is reduced due to the decreased blood flow and cyanosis appears, to measure a user's skin temperature.

The humidity measurement sensor 216 may be placed on the toe pulp tip and/or web space portion where skin temperature is reduced due to the decreased blood flow and cyanosis appears, to measure a user's skin humidity.

The pH measurement sensor 217 may be placed on a skin defect portion due to the diabetic foot wounds, to measure a pH of the skin defect portion.

The matrix metalloproteinase measurement sensor 218 may be placed on the skin defect portion due to the diabetic foot wounds, to measure a matrix metalloproteinase in the skin defect portion. According to one embodiment, the matrix metalloproteinase measurement sensor may measure the matrix metalloproteinase using the optical method.

The diabetic foot monitoring apparatus 110 according to an embodiment may check a degree of wound infection through a change in the pH, and monitor the wound state and healing ability through the matrix metalloproteinase using the pH measurement sensor 217 and/or the matrix metalloproteinase measurement sensor 218.

The improvement unit 220 may perform a function of improving the user's foot condition under the control of the controller 240. To this end, the improvement unit 220 may include a warmer 221, a blood flow promoter 222, and a pressure dispensing device 223.

The warmer 221 may apply heat to the foot by irradiating the user's foot with near-infrared rays. The warmer 221 may prevent peripheral blood vessel constriction and skin maceration due to a decrease in the skin temperature and an increase in the humidity through the near-infrared rays.

The blood flow promoter 222 may promote blood flow in the user's foot and induce tissue regeneration. For example, the blood flow promoter may induce tissue regeneration such as thermal effect, anti-inflammation, angiogenesis, and collagen formation by performing photodynamic therapy, far-infrared energy therapy, extracorporeal shockwave therapy and the like.

The pressure dispensing device 223 may generate vibrations in the diabetic foot monitoring apparatus 110 to disperse a pressure applied to the sole of the user's foot, or provide an alarm for inducing improvement of the user's posture and gait, or adding a pressure dispersion matrix or padding. In this case, the alarm may use a method of applying a low-frequency signal to a pressure overload portion, but it is not limited thereto, and various visual, auditory, and tactile methods may be used. Through this, it is possible to prevent joint deformity (Charcot joint) due to pressure overload in a specific portion, and hyperkeratosis and sequestration, which are factors that cause diabetic foot ulcers.

The communication unit 230 may perform communication with the diabetic foot analysis apparatus 120. Specifically, the communication unit 230 may transmit the user's foot condition information measured by the sensor unit 210 to the diabetic foot analysis apparatus 120 and receive a foot improvement control signal from the diabetic foot analysis apparatus 120.

According to one embodiment, the communication unit 230 may perform communication with the diabetic foot analysis apparatus 120 using a wired and/or wireless communication technique. In this case, the wireless communication technique may include Bluetooth communication, Bluetooth Low Energy (BLE) communication, Near Field Communication (NFC), wireless local area network (WLAN) communication, Zigbee communication, Infrared Data Association (IrDA) communication, Wi-Fi Direct (WFD) communication, ultra-wideband (UWB) communication, Ant+ communication, WIFI communication, Radio Frequency Identification (RFID) communication, 3G communication, 4G communication, 5G communication, or the like, but it is not limited thereto.

The controller 240 may control an overall operation of the diabetic foot monitoring apparatus 110. More specifically, the controller 240 may measure the user's foot condition information by controlling the sensor unit 210 periodically or when a predetermined event occurs. In addition, the controller 240 may control the improvement unit 220 according to the foot improvement control signal received from the diabetic foot analysis apparatus 120 to perform a function of improving the user's foot condition. According to one embodiment, the controller 240 may be formed of one or more processors or a combination of one or more processors and a memory.

According to one embodiment, the diabetic foot monitoring apparatus 110 may further include a storage unit 250.

The storage unit 250 may store programs or commands for operating the diabetic foot monitoring apparatus 110. In addition, the storage unit 250 may store the user's foot condition information measured by the sensor unit 210. In this case, the foot condition information may be stored in the storage unit together with additional information such as measurement date and measurement time.

According to one embodiment, the storage unit 250 may include at least one type of storage medium such as a flash memory type, a hard disk type, a multimedia card micro type, or a card type memory (e.g., SD or XD memory, etc.), Random Access Memory (RAM), Static Random Access Memory (SRAM), Read Only Memory (ROM), Electrically Erasable Programmable Read Only Memory (EEPROM), Programmable Read Only Memory (PROM), magnetic memory, magnetic disk, optical disk and the like. Further, the diabetic foot monitoring apparatus 110 may operate an external storage medium such as a web storage which performs the storage function of the storage unit 250 on the Internet.

The diabetic foot analysis apparatus 120 may determine the degree of progression of the user's diabetic foot ulcer based on the user's foot condition information, and may determine a method of improving foot conditions suitable for the user's foot condition information and the degree of progression of the diabetic foot ulcer. To this end, the diabetic foot analysis apparatus 120 may include a communication unit 310, a storage unit 320 and a processor 330.

The communication unit 310 may perform communication with the diabetic foot monitoring apparatus 110. Specifically, the communication unit 310 may receive the user's foot condition information from the diabetic foot monitoring apparatus 110 and transmit a foot improvement control signal according to the method of improving foot conditions to the diabetic foot monitoring apparatus 110.

According to one embodiment, the communication unit 310 may perform communication with the diabetic foot monitoring apparatus 110 using the above-described wired and/or wireless communication technique.

The storage unit 320 may store programs or commands for operating the diabetic foot analysis apparatus 120. In addition, the storage unit 320 may store the user's foot condition information received from the diabetic foot monitoring apparatus 110, and store the degree of progression of the diabetic foot ulcer determined by the processor 330 and the method of improving the foot condition. In this case, the foot condition information, the degree of progression of the diabetic foot ulcer, and the method of improving foot conditions may be stored in the storage unit together with additional information such as measurement date, measurement time, determination date, determination time and the like.

The storage unit 320 may store a diabetic foot determination model 321 for determining the degree of progression of the diabetic foot ulcer based on the user's foot condition information.

The diabetic foot determination model 321 may be established in advance using a machine learning algorithm. In this case, the machine learning algorithm may include a neural network, decision tree, genetic algorithm, genetic programming, Gaussian process regression, linear discriminant analysis, K-nearest neighbor, perceptron, radial basis function network, support vector machines, deep-learning (e.g., recurrent neural network (RNN), etc.) and the like. More preferably, the machine learning algorithm may be an RNN deep learning algorithm capable of performing real-time information processing and analysis.

The diabetic foot determination model 321 may be established in advance using foot condition information of a plurality of diabetic patients and degrees of progression of the diabetic foot ulcers corresponding thereto as learning data. Alternatively, the diabetic foot determination model 321 may be established in advance using the foot condition information of the plurality of diabetic patients, posture information at the time of measurement of the foot condition information, and the degrees of progression of the diabetic foot ulcers corresponding thereto as the learning data.

The processor 330 may perform pre-processing of the user's foot condition information and skin defect portion condition information received from the diabetic foot monitoring apparatus 110. In this case, the processor 330 may use various known preprocessing techniques.

The processor 330 may determine the degree of progression of the user's diabetic foot ulcer using the user's foot condition information and the diabetic foot determination model 321. In this case, the degree of progression of the diabetic foot ulcer may be classified into three stages, for example, danger, caution and normal, but it is not limited thereto.

The processor 330 may determine the method of improving foot conditions based on the user's foot condition information and the degree of progression of the diabetic foot ulcer, and may generate a message and/or a foot improvement control signal based on the determination.

For example, the processor 330 may continuously monitor a user's blood glucose level and observe a change in the blood glucose level during the day, thereby generating a message for inducing an improvement of dietary and lifestyle habits.

For another example, as a result of determination based on the pressure information applied to the sole of the user, if it is determined that there is a pressure overload portion, the processor 330 may generate a message for inducing an improvement in the patient's posture and gait, or an addition of a pressure dispersion mattress or padding to the pressure overload portion. In addition, the processor 330 may generate a foot improvement control signal for controlling the pressure dispensing device 223 of the diabetic foot monitoring apparatus 110 in order to disperse the pressure applied to the sole of the user's foot. In this case, the processor 330 may refer to the degree of progression of the diabetic foot ulcer. For example, the processor 330 may generate a foot improvement control signal only when the degree of progression of the diabetic foot ulcer is danger or caution, and may not generate the foot improvement control signal when the degree of progression of the diabetic foot ulcer is normal.

In addition, for another example, the processor 330 may generate a foot improvement control signal for controlling the warmer 221 and/or the blood flow promoter 222 of the diabetic foot monitoring apparatus 110 based on the blood flow information, transcutaneous oxygen saturation information, skin temperature information, and/or skin humidity information, which are measured from the user's foot. For example, if the blood flow or skin temperature is a predetermined threshold or less, or the transcutaneous oxygen saturation or skin humidity is a predetermined threshold or more, the processor 330 may generate a foot improvement control signal for controlling the warmer 221 and/or the blood flow promoter 222 of the diabetic foot monitoring apparatus 110 in order to prevent peripheral vasoconstriction and skin maceration, and promote the blood flow and tissue regeneration. In this case, the processor 330 may refer to the degree of progression of the diabetic foot ulcer. For example, the processor 330 may generate a foot improvement control signal only when the degree of progression of the diabetic foot ulcer is danger or caution, and may not generate the foot improvement control signal when the degree of progression of the diabetic foot ulcer is normal.

Detection values measured by the sensors of the sensor unit 210 of the diabetic foot monitoring apparatus 110 may be different according to the user's posture. Therefore, by using the user's posture information in determining the degree of progression of the diabetic foot ulcer, it is possible to improve the accuracy of determining the degree of progression of the diabetic foot ulcer. Here, the posture may include standing, sitting, walking, running and the like.

Therefore, according to an embodiment, the processor 330 may determine the user's posture, and determine the degree of progression of the user's diabetic foot ulcer by further using the determined user's posture.

For example, the processor 330 may determine the user's posture using the user's foot condition information, particularly pressure information, received from the diabetic foot monitoring apparatus 110. For another example, the processor 330 may determine the user's posture by asking the user about the current posture. However, this is only one embodiment but it is not limited thereto, and various known posture determination techniques may be used. In addition, the processor 330 may determine the degree of progression of the user's diabetic foot ulcer using the user's posture information, the user's foot condition information, and the diabetic foot determination model 321. In this case, the diabetic foot determination model 321 may be established in advance using foot condition information of a plurality of diabetic patients, posture information at the time of measuring the foot condition information, and degrees of progression of the diabetic foot ulcers corresponding thereto as the learning data.

According to one embodiment, the processor 330 may further use personal information (e.g., age, gender, etc.) and medical information of the user in determining the degree of progression of the user's diabetic foot ulcer and the method of improving foot conditions.

According to one embodiment, the diabetic foot analysis apparatus 120 may further include an input unit 340 and an output unit 350.

The input unit 340 may receive various operational signals and information input from the user. According to one embodiment, the input unit 340 may include a key pad, a dome switch, a touch pad, a jog wheel, a jog switch, a hardware/software (H/W) button or the like. In particular, when the touch pad forms a layer structure together with a display, it may be referred to as a touch screen.

The output unit 350 may output data, etc., which are input, stored, or processed in the diabetic foot analysis apparatus 120. For example, the output unit 350 may output the user's foot condition information received from the diabetic foot monitoring apparatus 110, the foot condition information determined by the processor 330, and the method of improving foot conditions, etc.

According to one embodiment, the output unit 350 may output data, etc., which are input, stored, or processed in the diabetic foot analysis apparatus 120 using at least one of an auditory method, a visual method and a tactile method. To this end, the output unit 350 may include a display, a speaker, a vibrator and the like.

Meanwhile, the blood glucose information measured by the diabetic foot monitoring apparatus 110 may be used to determine the number of prescriptions and an administration cycle of diabetes medications by a medical staff, and may also be used in cognitive behavioral therapy applications and software in conjunction with a user's mobile device.

The pressure information measured by the diabetic foot monitoring apparatus 110 may be used for analysis and correction of a user's daily gait posture. Weights may be reflected in the data of the pressure measurement sensor according to the position of each pressure measurement sensor.

The blood flow information and transcutaneous oxygen saturation information measured by the diabetic foot monitoring apparatus 110 may be used to determine the degree of peripheral vascular occlusion, to determine whether or not administer an agent for improving blood flow and whether or not perform surgery such as angioplasty, and to monitor a degree of blood flow improvement after surgery.

The pH information and matrix metalloproteinase information of the skin defect portion measured by the diabetic foot monitoring apparatus 110 may be used as data for identifying the condition of the diabetic foot wound, determining antibiotic administration or effect of wound healing promoter, and determining whether or not to need surgery including debridement.

Figure 4:
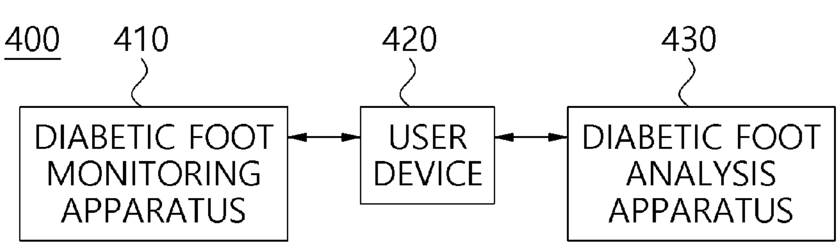
FIG. 4 is a block diagram illustrating another embodiment of the diabetic foot management system.
Figure 5:
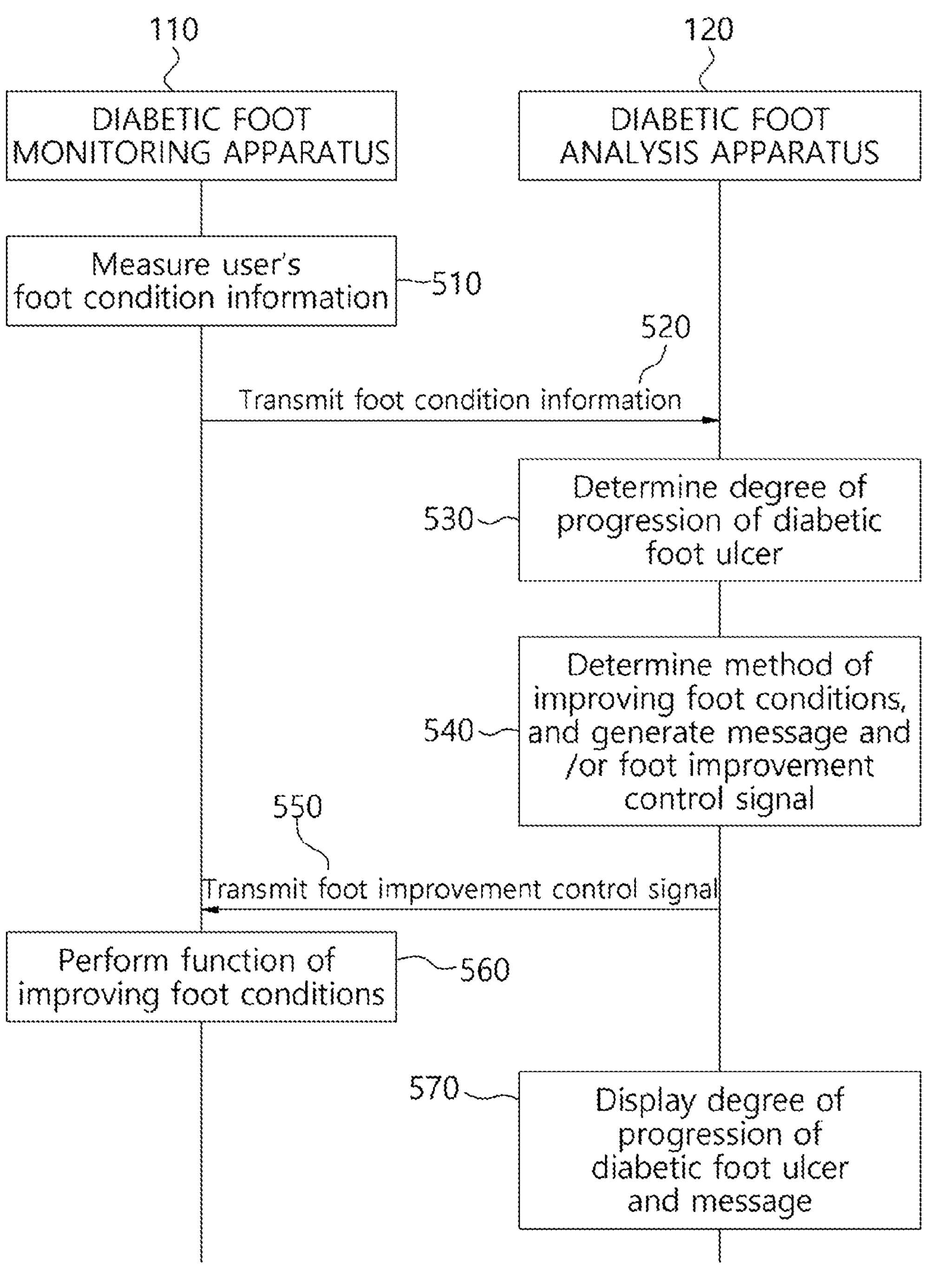
FIG. 5 is a flow chart illustrating an embodiment of a diabetic foot management method.
Figure 6:
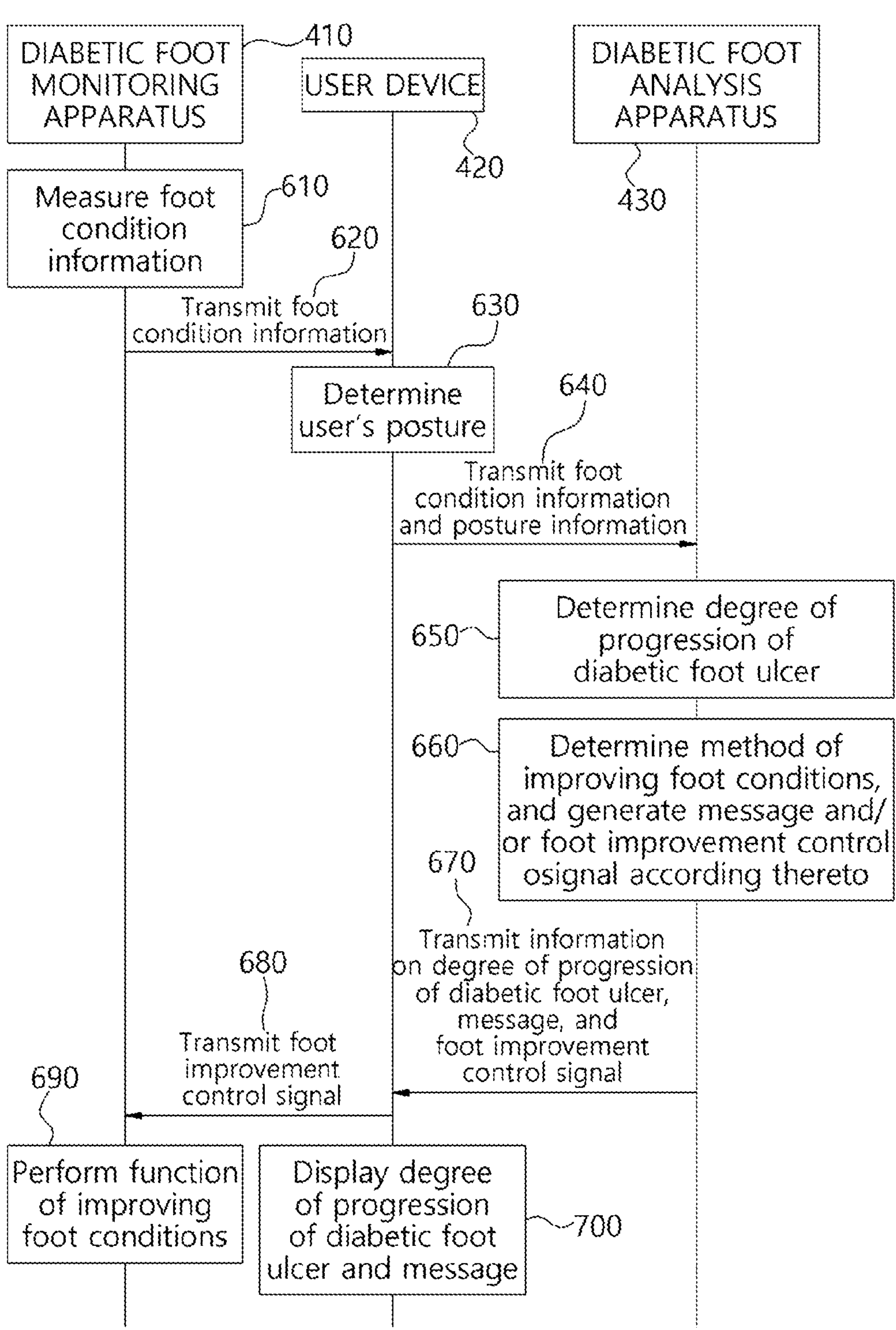
FIG. 6 is a flow chart illustrating another embodiment of the diabetic foot management method.

FIG. 4 is a block diagram illustrating another embodiment of the diabetic foot management system, FIG. 5 is a flow chart illustrating an embodiment of a diabetic foot management method, and FIG. 6 is a flow chart illustrating another embodiment of the diabetic foot management method using a diabetic foot analysis apparatus 430.

Referring to FIGS. 4 to 6, a diabetic foot management system 400 according to another embodiment may include a diabetic foot monitoring apparatus 410, a user device 420, and the diabetic foot analysis apparatus 430. The diabetic foot monitoring apparatus 410 and the diabetic foot analysis apparatus 430 are similar to the diabetic foot monitoring apparatus 110 and the diabetic foot analysis apparatus 120 described above with reference to FIGS. 1 to 3, and therefore will not be described in detail within the overlapping range.

The user device 420 is a device that is easy to carry and move, and may include a mobile phone, a smartphone, a tablet, a laptop computer, a personal digital assistant (PDA), a portable multimedia player (PMP), a navigation device, an MP3 player, a digital camera, a wearable device and the like. The wearable device may include a wristwatch type, a wrist band type, a ring type, a belt type, a necklace type, an ankle band type, a thigh band type, a forearm band type wearable device or the like. However, the electronic device is not limited to the above-described example, and the wearable device is also not limited to the above-described example.

The user device 420 may communicate with the diabetic foot monitoring apparatus 410 and the diabetic foot analysis apparatus 430. That is, unlike the diabetic foot monitoring apparatus 110 and the diabetic foot analysis apparatus 120 shown in FIGS. 1 to 3, the diabetic foot monitoring apparatus 410 and the diabetic foot analysis apparatus 430 do not directly communicate with each other, but may communicate indirectly through the user device 420.

The user device 420 may communicate with the diabetic foot monitoring apparatus 410 and the diabetic foot analysis apparatus 430, and may have a diabetic foot management application for managing diabetic feet installed therein.

The diabetic foot management application may receive the user's foot condition information from the diabetic foot monitoring apparatus 410 and transmit it to the diabetic foot analysis apparatus 430. In addition, the diabetic foot management application may receive the foot improvement control signal according to the method of improving foot conditions from the diabetic foot analysis apparatus 430 and transmit it to the diabetic foot monitoring apparatus 410.

According to one embodiment, the diabetic foot management application may determine the user's posture and transmit the determined posture information to the diabetic foot analysis apparatus 430. For example, the diabetic foot management application may determine the user's posture using the user's foot condition information, particularly pressure information, received from the diabetic foot monitoring apparatus 410. For another example, the diabetic foot management application may determine the user's posture by asking the user about the current posture.

The diabetic foot management application may receive information on the degree of progression of the user's diabetic foot ulcer from the diabetic foot analysis apparatus 430, and receive a message according to the method of improving foot conditions, to provide the received message to the user.

FIG. 5 is a flow chart illustrating an embodiment of the diabetic foot management method.

Referring to FIG. 5, the diabetic foot monitoring apparatus 110 is implemented as an insole type or a shoe type apparatus, and may measure user's foot condition information (510). Here, the foot condition information may include blood glucose information, pressure information, blood flow information, transcutaneous oxygen saturation (TcPO2) information, temperature information, humidity information, pH information, and matrix metalloproteinase information, which are measured at the user's foot.

The diabetic foot monitoring apparatus 110 may transmit the measured foot condition information to the diabetic foot analysis apparatus 120 (520). In this case, the diabetic foot monitoring apparatus 110 may use the above-described wired and/or wireless communication technique.

The diabetic foot analysis apparatus 120 may determine the degree of progression of the user's diabetic foot ulcer based on the received foot condition information (530).

For example, the diabetic foot analysis apparatus 120 may determine the degree of progression of the user's diabetic foot ulcer using the user's foot condition information and the diabetic foot determination model. In this case, the diabetic foot determination model may be established in advance using a machine learning algorithm. The machine learning algorithm may include a neural network, decision tree, genetic algorithm, genetic programming, Gaussian process regression, linear discriminant analysis, K-nearest neighbor, perceptron, radial basis function network, support vector machines, deep-learning (e.g., recurrent neural network (RNN), etc.) and the like. More preferably, the machine learning algorithm may be an RNN deep learning algorithm capable of performing real-time information processing and analysis. The diabetic foot determination model may be established in advance using foot condition information of a plurality of diabetic patients and degrees of progression of the diabetic foot ulcers corresponding thereto as the learning data.

For another example, the diabetic foot analysis apparatus 120 may determine the user's posture, and determine the degree of progression of the user's diabetic foot ulcer using the user's foot condition information, posture information, and the diabetic foot determination model. In this case, the diabetic foot determination model is a machine learning-based model, and may be established in advance using the foot condition information of the plurality of diabetic patients, posture information at the time of measurement of the foot condition information, and the degrees of progression of the diabetic foot ulcers corresponding thereto as the learning data.

The diabetic foot analysis apparatus 120 may determine the method of improving foot conditions based on the user's foot condition information and the degree of progression of the diabetic foot ulcer, and may generate a message and/or a foot improvement control signal based on the determination (540).

For example, the diabetic foot analysis apparatus 120 may continuously monitor a user's blood glucose level and observe a change in the blood glucose level during the day, thereby generating a message for inducing an improvement of dietary and lifestyle habits.

For another example, as a result of determination based on the pressure information applied to the sole of the user, if it is determined that there is a pressure overload portion, the diabetic foot analysis apparatus 120 may generate a message for inducing an improvement in the patient's posture and gait, or an addition of a pressure dispersion mattress or padding to the pressure overload portion. In addition, the diabetic foot analysis apparatus 120 may generate a foot improvement control signal for controlling the pressure dispensing device of the diabetic foot monitoring apparatus 110 in order to disperse the pressure applied to the sole of the user's foot. In this case, the diabetic foot analysis apparatus 120 may refer to the degree of progression of the diabetic foot ulcer.

In addition, for another example, the diabetic foot analysis apparatus 120 may generate a foot improvement control signal for controlling the warmer and/or the blood flow promoter of the diabetic foot monitoring apparatus 110 based on the blood flow information, transcutaneous oxygen saturation information, skin temperature information, and/or skin humidity information, which are measured from the user's foot. For example, if the blood flow or skin temperature is a predetermined threshold or less, or the transcutaneous oxygen saturation or skin humidity is a predetermined threshold or more, the diabetic foot analysis apparatus 120 may generate a foot improvement control signal for controlling the warmer and/or the blood flow promoter of the diabetic foot monitoring apparatus 110 in order to prevent peripheral vasoconstriction and skin maceration and promote the blood flow and tissue regeneration. In this case, the diabetic foot analysis apparatus 120 may refer to the degree of progression of the diabetic foot ulcer.

The diabetic foot analysis apparatus 120 may transmit the generated foot improvement control signal to the diabetic foot monitoring apparatus 110 (550).

The diabetic foot monitoring apparatus 110 may perform a function of improving foot conditions based on the foot improvement control signal received from the diabetic foot analysis apparatus 120 (560).

For example, the diabetic foot monitoring apparatus 110 may: apply heat to the foot by irradiating the user's foot with near-infrared rays; induce tissue regeneration such as thermal effect, anti-inflammation, angiogenesis, and collagen formation by performing photodynamic therapy, far-infrared energy therapy, extracorporeal shockwave therapy and the like; generate vibrations to disperse a pressure applied to the sole of the user's foot; or provide an alarm for inducing improvement of the user's posture and gait, or adding a pressure dispersion matrix or padding.

The diabetic foot analysis apparatus 120 may display the degree of progression of the diabetic foot ulcer and the message (570).

FIG. 6 is a flow chart illustrating another embodiment of the diabetic foot management method.

Referring to FIG. 6, the diabetic foot monitoring apparatus 410 is implemented as an insole type or a shoe type apparatus, and may measure user's foot condition information (610), then transmit the measured foot condition information to the user device 420 (620).

The user device 420 may receive the foot condition information from the diabetic foot monitoring apparatus 410 and determine the user's posture (630). For example, the user device 420 may determine the user's posture using the user's foot condition information, particularly pressure information, received from the diabetic foot monitoring apparatus 410. For another example, the user device 420 may determine the user's posture by asking the user about the current posture. However, this is only one embodiment but it is not limited thereto, and various known posture determination techniques may be used.

The user device 420 may transmit the foot condition information and posture information to the diabetic foot analysis apparatus 430 (640).

The diabetic foot analysis apparatus 430 may determine the degree of progression of the user's diabetic foot ulcer using the user's foot condition information, posture information, and the diabetic foot determination model (650). In this case, the diabetic foot determination model is a machine learning-based model, and may be established in advance using foot condition information of a plurality of diabetic patients, posture information at the time of measurement of the foot condition information, and the degrees of progression of the diabetic foot ulcers corresponding thereto as the learning data.

The diabetic foot analysis apparatus 430 may determine a method of improving foot conditions based on the user's foot condition information and the degree of progression of the diabetic foot ulcer, and may generate a message and/or a foot improvement control signal according thereto based on the determination (660).

The diabetic foot analysis apparatus 430 may transmit information on the degree of progression of the diabetic foot ulcer, the message, and the foot improvement control signal to the user device 420 (670).

The user device 420 may receive the diabetic foot progress information, the message, and the foot improvement control signal, and transmit the foot improvement control signal to the diabetic foot monitoring apparatus 410 (680).

The diabetic foot monitoring apparatus 410 may receive the foot improvement control signal from the user device 420, and perform a function of improving the foot conditions based on the received foot improvement control signal (690).

The user device 420 may display the degree of progression of the diabetic foot ulcer and the message (700).

An aspect of the present invention may be implemented as computer readable code on a computer readable recording medium. Codes and code segments implementing the above program may be easily inferred by a computer programmer in the art. A computer-readable recording medium may include all types of recording devices storing data that may be read by a computer system. Examples of computer-readable recording media may include ROM, RAM, CD-ROM, magnetic tape, floppy disk, optical disk and the like. In addition, the computer-readable recording medium may be distributed among computer systems connected through a network, and may be written and executed as computer-readable codes in a distributed manner.

So far, the present invention has been looked at mainly with its preferred embodiments. Those of ordinary skill in the art to which the present invention pertains will understand that the present invention may be implemented in a modified form without departing from the essential characteristics of the present invention. Therefore, the scope of the present invention should be construed to include various embodiments within the scope equivalent to those described in the claims without being limited to the above-described embodiments.

What is claimed is:

1. A diabetic foot management system comprising:

a diabetic foot monitoring apparatus configured to measure foot condition information of a user; and a diabetic foot analysis apparatus configured to determine the user's posture, and to determine a degree of progression of the user's diabetic foot ulcer from the measured foot condition information and the determined posture using a machine learning-based diabetic foot determination model, and to generate a foot improvement control signal for controlling the diabetic foot monitoring apparatus, and wherein the diabetic foot monitoring apparatus comprises a blood glucose measurement sensor, a pressure measurement sensor, a blood flow measurement sensor, a transcutaneous oxygen saturation measurement sensor, a temperature measurement sensor, a humidity measurement sensor, a pH measurement sensor, and a matrix metalloproteinase measurement sensor, wherein the blood glucose measurement sensor, the blood flow measurement sensor, and the transcutaneous oxygen saturation measurement sensor are disposed on a longitudinal arch portion of the user's foot, the pressure measurement sensor is disposed on a heel portion of a sole or both sides of the front portion including a greater ball portion and a lesser ball portion, the temperature measurement sensor and the humidity measurement sensor are disposed in a web space portion between toes of the user's foot, and the pH measurement sensor and the matrix metalloproteinase measurement sensor are disposed on a skin defect portion caused by diabetic foot wounds, and wherein the diabetic foot monitoring apparatus further comprises a pressure dispensing device configured to apply a low-frequency signal to a pressure overload portion to provide an alarm, and to generate vibration to disperse pressure applied to the sole of the user's foot in response to the foot improvement control signal.

2. The diabetic foot management system according to claim 1, wherein the blood glucose measurement sensor measures blood glucose using user's sweat.

3. The diabetic foot management system according to claim 1, wherein the diabetic foot monitoring apparatus comprises at least one of a warmer configured to apply heat to the user's foot, and a blood flow promoter configured to promote blood flow in the user's foot.

4. The diabetic foot management system according to claim 3, wherein the diabetic foot analysis apparatus generates a foot improvement control signal for controlling the warmer, the blood flow promoter, and the pressure dispensing device based on the user's foot condition information and the degree of progression of the diabetic foot ulcer.

5. The diabetic foot management system according to claim 1, wherein the diabetic foot monitoring apparatus is implemented as an insole type or a shoe type apparatus.

6. The diabetic foot management system according to claim 1, wherein the posture includes standing, sitting, walking, and running.

7. The diabetic foot management system according to claim 1, wherein the diabetic foot analysis apparatus determines the user's posture using the user's foot condition information.

8. A diabetic foot analysis apparatus comprising:

a communication unit configured to receive foot condition information of a user from a diabetic foot monitoring apparatus;

a storage unit configured to store a machine learning-based diabetic foot determination model; and a processor configured to determine the user's posture, and to determine a degree of progression of the user's diabetic foot ulcer based on the received foot condition information and the determined posture using the diabetic foot determination model, wherein the foot condition information comprises blood glucose information, pressure information, blood flow information, transcutaneous oxygen saturation (TcPO2) information, temperature information, humidity information, pH information, and matrix metalloproteinase information, which are measured from a user's foot, wherein the blood glucose information, the blood flow information, and the transcutaneous oxygen saturation information are measured at a longitudinal arch portion of the user's foot, the pressure information is measured at a heel portion of the sole or both sides of a forefoot portion including a greater ball portion and a lesser ball portion, the temperature information and the humidity information are measured at a web space portion between toes of the user's foot, and the pH information and the matrix metalloproteinase information are measured at a skin defect portion caused by diabetic foot wounds, wherein the processor is configured to generate a foot improvement control signal for controlling the diabetic foot monitoring apparatus to apply a low-frequency signal to a pressure overload portion to provide an alarm and to generate vibration to disperse pressure applied to the sole of the user's foot.

9. The diabetic foot analysis apparatus to claim 8, wherein the posture includes standing, sitting, walking, and running.

10. The diabetic foot analysis apparatus to claim 8, wherein the processor determines the user's posture using the user's foot condition information.

11. The diabetic foot analysis apparatus to claim 8, wherein the diabetic foot determination model is established using foot condition information of a plurality of diabetic patients, posture information measured at the time when foot condition information is measured, and degrees of progression of the diabetic foot ulcers corresponding thereto as learning data.

* * * * *